(12) United States Patent
Moore et al.

(10) Patent No.: US 12,383,258 B2
(45) Date of Patent: Aug. 12, 2025

(54) EIGHT-DIMENSIONAL BARBED SURGICAL THREAD

(71) Applicant: Eurothreads LLC, Hudson, WI (US)

(72) Inventors: Tamara Moore, Hudson, WI (US); Laurie Wall, Hudson, WI (US)

(73) Assignee: Eurothreads LLC, Cheyenne, WY (US)

( * ) Notice: Subject to any disclaimer, the term of this patent is extended or adjusted under 35 U.S.C. 154(b) by 995 days.

(21) Appl. No.: 17/017,493

(22) Filed: Sep. 10, 2020

(65) Prior Publication Data

US 2021/0068825 A1 Mar. 11, 2021

Related U.S. Application Data

(60) Provisional application No. 62/901,596, filed on Sep. 17, 2019, provisional application No. 62/898,174, filed on Sep. 10, 2019.

(51) Int. Cl.
*A61B 17/06* (2006.01)
*A61B 17/00* (2006.01)
*A61L 17/12* (2006.01)

(52) U.S. Cl.
CPC .. *A61B 17/06166* (2013.01); *A61B 17/06066* (2013.01); *A61L 17/12* (2013.01); *A61B 2017/00792* (2013.01); *A61B 2017/00796* (2013.01); *A61B 2017/06176* (2013.01); *A61L 2430/34* (2013.01)

(58) Field of Classification Search
CPC .... A61B 17/06166; A61B 2017/06176; A61B 2017/00792; A61B 2017/00796; A61B 17/06066; A61L 2430/34
See application file for complete search history.

(56) References Cited

U.S. PATENT DOCUMENTS

| | | | |
|---|---|---|---|
| 6,551,343 B1 | 4/2003 | Tormala | |
| 7,070,610 B2 | 7/2006 | Im | |
| 2004/0060409 A1* | 4/2004 | Leung | A61B 17/04 83/522.14 |
| 2007/0156161 A1* | 7/2007 | Weadock | A61M 1/895 606/170 |
| 2008/0027486 A1* | 1/2008 | Jones | A61F 2/12 606/228 |
| 2011/0125188 A1* | 5/2011 | Goraltchouk | D01F 6/00 606/228 |

(Continued)

FOREIGN PATENT DOCUMENTS

WO WO-2019068928 A1 * 4/2019 ....... A61B 17/06066

OTHER PUBLICATIONS

International Search Report and Written Opinion Received for PCT/US2020/050238 on Nov. 23, 2020, 11 pgs.

(Continued)

*Primary Examiner* — Elizabeth Houston
*Assistant Examiner* — Serenity A Miller (57) ABSTRACT

An eight-dimensional barbed surgical thread including a central core and eight first barbs. The central core has a circumference, a proximal end and a distal end that is opposite the proximal end. The eight first barbs are positioned around the circumference of the central core so that the first barbs are radially adjacent to each other and obliquely extend from the central core.

14 Claims, 5 Drawing Sheets

(56) References Cited

U.S. PATENT DOCUMENTS

2013/0238021 A1* 9/2013 Gross .............. A61B 17/06166
606/228
2017/0119370 A1* 5/2017 Hong .............. A61B 17/06166
2018/0078355 A1 3/2018 Kim
2018/0177505 A1 6/2018 Chu
2018/0317912 A1 11/2018 Brandi

OTHER PUBLICATIONS

International Search Report and Written Opinion Received for PCT/US2020/050239 on Nov. 23, 2020, 11 pgs.

* cited by examiner

EIGHT-DIMENSIONAL BARBED SURGICAL THREAD

REFERENCE TO RELATED APPLICATION

This application claims priority to U.S. Applic. No. 62/898,174, which was filed on Sep. 10, 2019. The contents of which are incorporated herein by reference.

FIELD OF THE INVENTION

The invention relates generally to thread for surgical applications. More particularly, the invention relates to eight-dimensional barbed surgical thread.

BACKGROUND OF THE INVENTION

A variety of aesthetic medical techniques have been developed to enhance the appearance of a person's skin and, in particular, the appearance of the person's face. These techniques range from cutting and tightening of the skin to injecting compositions into the skin such as to reduce wrinkles. Despite these advances, there is a continuing need to non-surgical techniques to improve a person's appearance.

SUMMARY OF THE INVENTION

An embodiment of the invention is directed to an eight-dimensional barbed surgical thread that includes a central core and eight first barbs. The central core has a circumference, a proximal end and a distal end that is opposite the proximal end. The eight first barbs are positioned around the circumference of the central core so that the first barbs are radially adjacent to each other and obliquely extend from the central core.

Another embodiment of the invention is directed to an eight-dimensional barbed surgical thread that includes a central core, eight first barbs and eight second barbs. The central core has a circumference, a proximal end and a distal end that is opposite the proximal end. The eight first barbs are positioned around the circumference of the central core and obliquely extend from the central core. Each of the eight first barbs has a distal end and a proximal end. The distal end of one of the first barbs is closer to the proximal end of the central core than the proximal end of the one of the second barbs. The eight second barbs are positioned around the circumference of the central core and obliquely extend from the central core. The eight second barbs are closer to the proximal end than the eight first barbs. Each of the eight second barbs has a distal end and a proximal end. The distal end of one of the second barbs is closer to the distal end of the central core than the proximal end of the one of the second barbs.

Another embodiment of the invention is directed to a method of using an eight-dimensional barbed surgical thread. An eight-dimensional barbed surgical thread is provided that includes a central core, eight first barbs and eight second barbs. The central core has a circumference, a proximal end and a distal end that is opposite the proximal end. The eight first barbs are positioned around the circumference of the central core and obliquely extend from the central core. Each of the eight first barbs has a distal end and a proximal end. The distal end of one of the first barbs is closer to the proximal end of the central core than the proximal end of the one of the second barbs. The eight second barbs are positioned around the circumference of the central core and obliquely extend from the central core. The eight second barbs are closer to the proximal end than the eight first barbs. Each of the eight second barbs has a distal end and a proximal end. The distal end of one of the second barbs is closer to the distal end of the central core than the proximal end of the one of the second barbs. The eight-dimensional barbed surgical thread is inserted into a dermis on a patient. The eight first barbs engage the dermis to lift the dermis to a lifted position. The eight second barbs engage the dermis to anchor the dermis in the lifted position.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
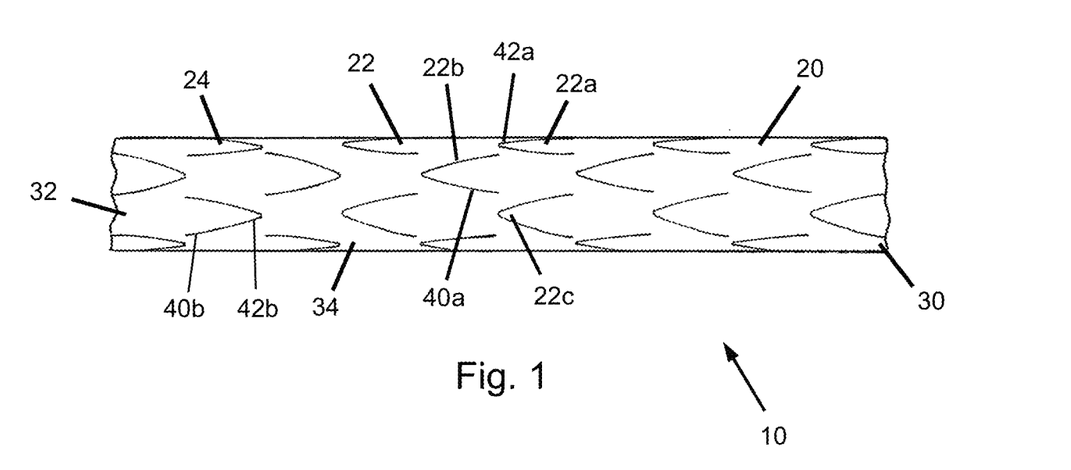
FIG. 1 is a side view of an eight-dimensional barbed surgical thread according to an embodiment of the invention.

The invention is directed to an eight-dimensional barbed surgical thread as illustrated at 10 in FIG. 1. The eight-dimensional barbed surgical thread 10 is particularly suited for use in cosmetic enhancement procedures. The eight-dimensional barbed surgical thread 10 includes a central core 20 from which a plurality of first barbs 22 extend.

An advantage of the eight-dimensional barbed surgical thread 10 over the prior art barbed surgical threads is that the eight-dimensional barbed surgical thread 10 of this invention produces multiple effects once introduced into the dermis.

These effects fall into three major categories: (1) instant skin lifting through mechanical effects, (2) cellular renewal through collagen stimulation and neovascularization to improve skin texture, fine lines and elasticity, and (3) skin tightening by contracting fat tissue.

The eight-dimensional barbed surgical thread 10 is a medical device that in certain embodiments consists of a monofilament surgical suture. The eight-dimensional barbed surgical thread 10 may be fabricated from a variety of materials. In certain embodiments, the materials used to fabricate the eight-dimensional barbed surgical thread are absorbable inside of a human body. A non-limiting example of a suitable material for fabricating the eight-dimensional barbed surgical thread 10 is a polydioxanone (PDO)/polycaprolacton (PCL) polymer.

Figure 2:
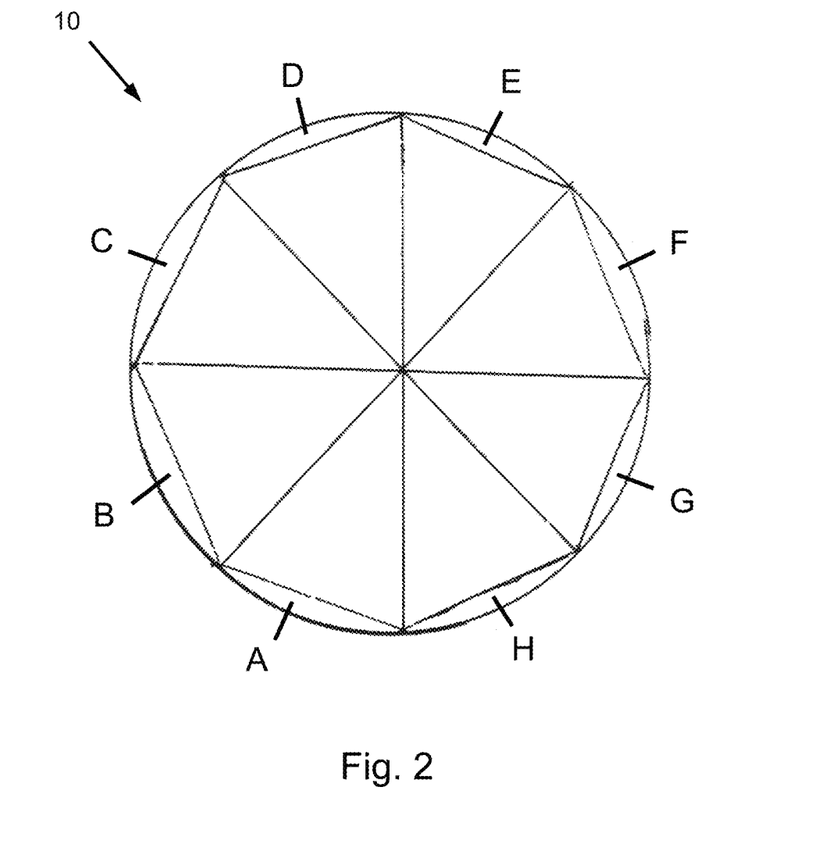
FIG. 2 is a cross-sectional overview of the eight-dimensional barbed surgical thread.
Figure 3:
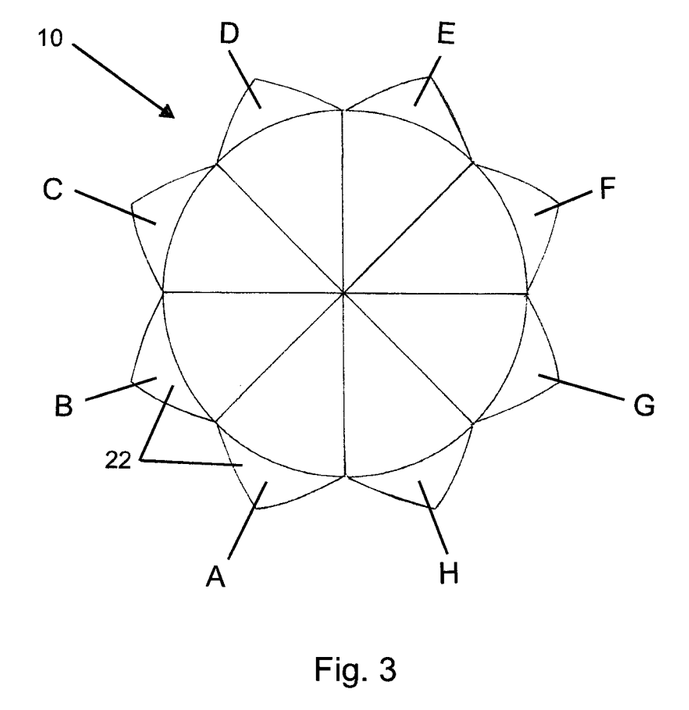
FIG. 3 is a cross-sectional view of the eight-dimensional barbed surgical thread illustrating locations of barbs extending therefrom.

In certain embodiments, a cut is used to form each of the first barbs 22. A variety of cutting techniques may be used. In certain embodiments, the eight-dimensional barbed surgical thread 10 is fabricated by laser cutting into the surgical suture octagonally at an angle of about 45 degree as illustrated in FIG. 2. The locations of the eight cuts is indicated by letters A-H.

Using such a configuration, the eight first barbs 22 are radially adjacent to each other when going around a circumference of the eight-dimensional barbed surgical thread 10. While in certain embodiments, the first barbs 22 are immediately radially adjacent to each other such as illustrated in FIG. 2, it is possible that there can be a spacing between adjacent first barbs 22. As used herein, the spacing between adjacent first barbs 22 is less than about 20 percent of the width of the widest portion of the first barbs 22. In other embodiments, the spacing between adjacent first barbs 22 is less than about 10 percent of the width of the widest portion of the first barbs 22.

Using the preceding configuration enhances the potential of contacts between the first barbs 22 after insertion into the dermis regardless of the orientation of the eight-dimensional barbed surgical thread 10, which reduces the potential of the dermis sagging after insertion of the eight-dimensional barbed surgical thread 10.

The cutting that is done to form the first barb 22 is done at an angle to the surface of the central core 20. In certain configurations, the first barbs 22 are oblique, notched protrusions formed into a surgical suture at an angle of between about 10 degrees and about 15 degrees. In other embodiments, the angle of the cut to form the first barb 22 is about 12.5 degrees. Cutting in this manner causes a width of the first barb 22 decreases when moving from the proximal end 40a to the distal end 42a. In certain embodiments, the distal end 42a of the first barb 22 is pointed.

In certain embodiments, a ratio of a length of the barb to a width of the barb is between about 2:1 and about 5:1. Forming the first barbs 22 with the length to width ratio in this range provides the first barbs 22 with sufficient strength for the first barbs 22 to perform the desired functions during the insertion process and after insertion.

Adjacent first barbs 22 may be offset in a direction moving from a distal end 32 to a proximal end 30 of the central core 20 as illustrated in FIG. 1. In one such embodiment, a distal end 42a of one first barb 22a is approximately aligned with a proximal end 40a of an adjacent first barb 22b around a circumference of the central core 20, as illustrated in FIG. 1. Additionally, the distal end 42a of every other first barb 22a, 22c is approximately aligned around a circumference of the central core 20, as illustrated in FIG. 1.

The first barbs 22 have a proximal end 40a and a distal end 42a. The proximal end 40a is where the first barb 22 attaches to the central core 20. The distal end 42a is opposite the proximal end 40.

The plurality of first barbs 22 are cut at intervals of about 45 degrees on eight sides of the eight-dimensional barbed surgical thread 10. In certain embodiments, the distance between adjacent first barbs 22 is about 1.5 millimeters, which is closer than the conventional spacing of about 1.8 millimeters that is used in the prior art surgical thread that is used when performing facelifts.

The plurality of first barbs 22 are oriented such that the distal end 42a of each first barb 22 is closer to the central core distal end 32 than the proximal end 40a of each first barb 22. As described in more detail below, a primary function of the plurality of first barbs 22 is lifting.

In certain embodiments, the plurality of first barbs 22 occupy greater than about ½ of a length of the eight-dimensional barbed surgical thread 10. In other embodiments, the plurality of first barbs 22 occupy about ⅔ of the length of the eight-dimensional barbed surgical thread 10.

The eight-dimensional barbed surgical thread 10 is typically inserted so that the plurality of first barbs 22 are facing upwardly. The configuration of the plurality of first barbs 22 on the eight-dimensional barbed surgical thread 10 thereby allows for most of the eight-dimensional barbed surgical thread 10 to assist in lifting of the tissue.

The eight-dimensional barbed surgical thread 10 also includes a plurality of second barbs 24 proximate the central core distal end 32. The eight-dimensional barbed surgical thread 10 is typically inserted so that the plurality of second barbs 24 are facing downwards. As described in more detail below, a primary function of the plurality of second barbs 24 is anchoring.

The plurality of second barbs 24 are cut at intervals of about 45 degrees on eight sides of the eight-dimensional barbed surgical thread 10. In certain embodiments, the distance between adjacent second barbs 24 is about 1.5 millimeters, which is closer than the conventional spacing of about 1.8 millimeters that is used in the prior art surgical thread that is used when performing facelifts.

Other than the orientation, the second barbs 24 may be shaped similarly to the first barbs 22. The plurality of second barbs 24 are oriented such that the distal end 42b of each second barb 24 is closer to the distal central core proximal end 30 than the distal proximal end 40b of each second barb 24.

In certain embodiments, the plurality of second barbs 24 occupies less than about ½ of the length of the eight-dimensional barbed surgical thread 10. In other embodiments, the plurality of second barbs 24 occupies about ⅓ of the length of the eight-dimensional barbed surgical thread 10.

In certain embodiments, there may be an intermediate region 34 of the eight-dimensional barbed surgical thread 10 that is intermediate the upwardly facing first barbs 22 and the downwardly facing second barbs 24 from which no barbs extend therefrom. This intermediate region 34 on the eight-dimensional barbed surgical thread 10 may have a length that is smaller than the length of the eight-dimensional barbed surgical thread 10 over which the upwardly extending first barbs 22 extend. The length of the intermediate region of the eight-dimensional barbed surgical thread 10 may be smaller than the length of the eight-dimensional barbed surgical thread 10 over which the downwardly extending second barbs 24 extend.

Unlike the prior art two-dimensional, three-dimensional and four-dimensional barbed surgical thread that limited the ability to engage tissue, the eight-dimensional barbed surgical thread 10 of this invention significantly improves the viability and uniformity of tissue engagement thus the sustainability of the desired result.

Additionally, upon insertion of the eight-dimensional barbed surgical thread 10 into the dermis, the dermis sustains minor injuries. These minor injuries engage the body's natural healing process and stimulate the skin cells to produce collagen and blood vessels, which improves skin microcirculation.

It has been found that in areas of the body that do not have bone structure beneath, such as the fatty area of the cheek, having more points of tissue attachment provides a greater degree of lift, greater points of injury and a larger amount of fiberblasting, which thereby results in greater collagen production.

The eight-dimensional barbed surgical 10 is inserted into the subcutaneous layer of the dermis. In certain embodiments, a cannula is used to insert the eight-dimensional barbed surgical thread 10 into the dermis. In other embodiments, the cannula is a rounded or L-tipped surgical steel cannula.

The eight-dimensional barbed surgical thread 10 is not attached to the surgical cannula and is introduced into the soft tissue through the tip of the cannula. Once the cannula reaches the desired end site, the cannula is rotated about 180 degrees mechanically engaging the eight-dimensional barbed surgical thread 10 at the distal (lower) end.

The cannula is then removed leaving only the eight-dimensional barbed surgical thread 10 in the dermis. Approximating the tissue up the eight-dimensional barbed surgical thread 10 (lifting the tissue onto each barb) allows for each of the first barbs 22 to become securely engaged in the dermis. Once the desired result is achieved, the eight-dimensional barbed surgical thread 10 is anchored at the proximal (upper) end. Any excess portion of the eight-dimensional barbed surgical thread 10 is cut off and discarded.

The use of eight-dimensional barbed surgical threads 10 is indicated for soft tissue augmentation where the insertion of surgical sutures is appropriate. The eight-dimensional barbed surgical threads 10 are used to lift, contour and volumize the skin. The implantation of the eight-dimensional barbed surgical threads 10 is indicated for subcutaneous (intradermal and hypodermal) implantation.

In operation, once the area to be treated is defined, and an appropriate examination is completed, the patient is seated. The treatment area should be prepped by cleansing and removing the topical anesthetic. If topical anesthetic is to be used, it is applied liberally to the treatment areas.

The appropriate thread packages required for the treatment area are opened and removed from the package. The thread is attached in accordance with the manufacturer's instructions. Proper use of the product should minimize the chances of dislodging or breaking while injecting the thread.

Correct injection technique is important to the success of the treatment in achieving the desired results. The needle or cannula should be inserted into the treatment site with the tip ending up at an appropriate depth within the skin. The eight-dimensional barbed surgical thread 10 should then be released using a slow, steady withdrawal of the needle/cannula. Overcorrection, which is more threads than suggested or required, is generally not needed and is to be avoided.

Once the first thread is appropriately inserted, another thread is inserted into the next adjacent location, and the process is repeated. Care should be taken to adequately assess the entire area to be treated with the correct number of threads to ensure even and symmetrical distribution of the product.

Once the injection is completed, the treated areas should be gently massaged, setting the threads per instruction. More vigorous massage may result in additional swelling, bruising or dislodgement of the thread.

Unlike the prior art two-dimensional, three-dimensional and four-dimensional barbed surgical threads that are limited in their ability to engage tissue due to barbs being cut respectively on only 2, 3 or 4 sides of the thread. This greatly limits the number of points of engagement into soft tissue. It is this engagement that is necessary to achieve a sustainable lift.

With eight-dimensional barbed surgical threads 10, the presence of additional first barbs 22 more than double the points of tissue engagement of the four-dimensional barbed surgical thread. Regardless of how the eight-dimensional barbed surgical thread 10 is inserted into subcutaneous tissue, the additional first barbs 22 allows the eight-dimensional barbed surgical thread 10 to grab onto additional dermis resulting in a better lift.

The eight-dimensional barbed surgical thread that is fabricated from PDO alone or in combination with PCL is slowly absorbed after implantation into the patient. In certain embodiments, the eight-dimensional barbed surgical thread is resorbed over a time period of between about 180 days and about 240 days. After this time period, the eight-dimensional barbed surgical thread 10 is substantially absorbed into the surrounding tissue. As used herein, substantially absorbed means that there are only minimal traces remaining of the eight-dimensional barbed surgical thread 10.

Examples

In the following example, the performance of the eight-dimensional barbed surgical thread according to this invention is evaluated. The subject on which the procedure was performed is a 60+-year-old Caucasian man. The subject complained of sagging skin such as on his chest.

The concerns of the male subject are similar to the concerns of many 60 to 70 year old men.

Figure 4:
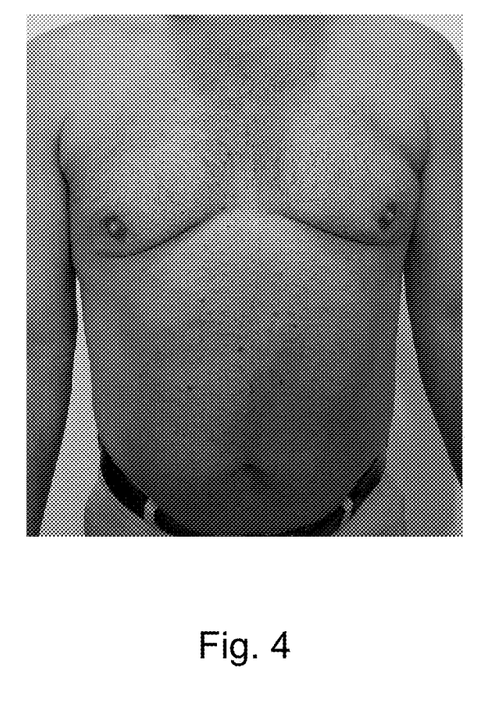
FIG. 4 is a front view before a procedure using the eight-dimensional barbed surgical thread.
Figure 5:
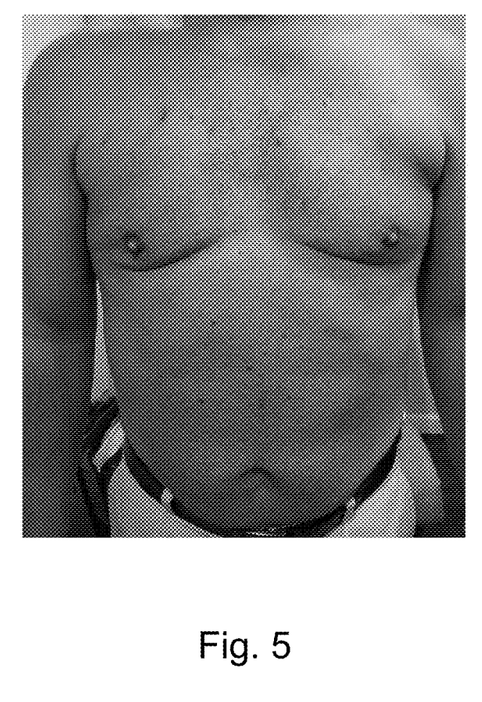
FIG. 5 is a front view after the procedure using the eight-dimensional barbed surgical thread.
Figure 6:
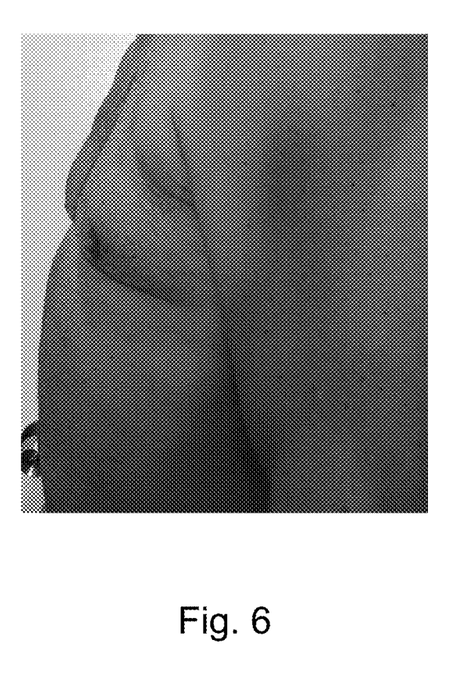
FIG. 6 is a side view before the procedure using the eight-dimensional barbed surgical thread.
Figure 7:
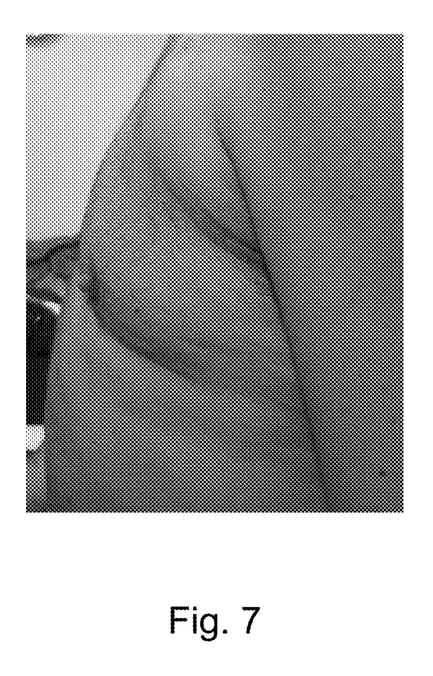
FIG. 7 is a side view after the procedure using the eight-dimensional barbed surgical thread.

FIGS. 4 and 5 are before and after front photographs, respectively, of a male subject on which mastopexy was performed while FIGS. 6 and 7 are before and after side photographs, respectively of the male subject on which the mastopexy was performed.

Figure 8:
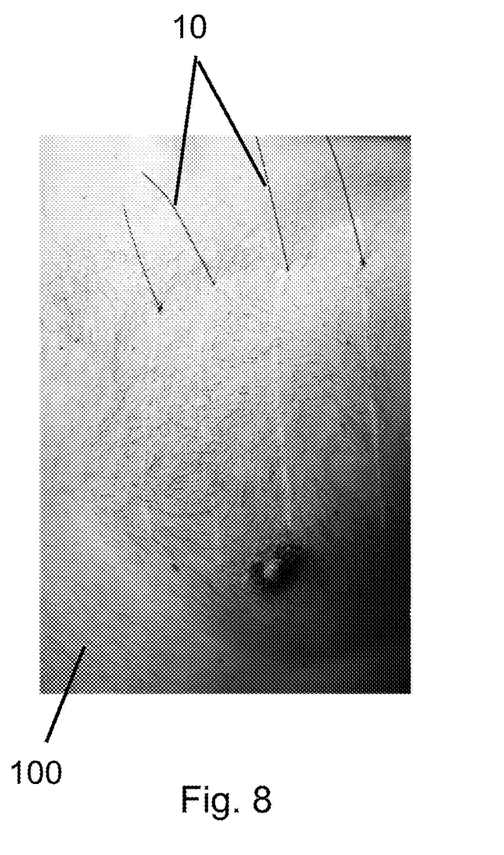
FIG. 8 is a front view after insertion of the eight-dimensional barbed surgical thread.
Figure 9:
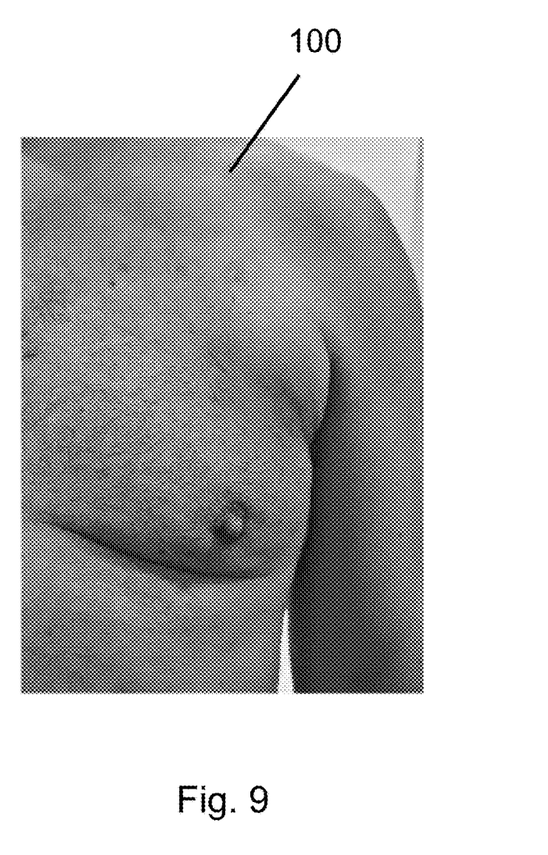
FIG. 9 is front view after trimming of the eight-dimensional barbed surgical thread.

FIG. 8 illustrates proximal ends of the eight-dimensional barbed surgical threads 10 extending from the patient 100. After the proximal ends of the eight-dimensional barbed surgical threads 10 are trimmed, the final lifted results are illustrated in FIG. 9.

Cosmetic medical procedures were conducted to evaluate the performance of the eight-dimensional barbed surgical thread of this application to the prior art four-dimensional barbed surgical thread as well as to a six-dimensional barbed surgical thread that is the subject of a separate patent application that is being filed on the same day as this patent application.

The performance of the respective surgical threads as evaluated with respect to lifting of the dermis and stimulating collagen production. The relative performance of the six-dimensional barbed surgical thread and the eight-dimensional barbed surgical thread with respect to the prior art four-dimensional barbed surgical thread was classified as either no change, minimal change, moderate change and significant change from the perspective of an experienced medical practitioner in the field of cosmetic medical procedures.

The results from the use of the six-dimensional barbed surgical thread, the eight-dimensional barbed surgical thread and the prior art four-dimensional barbed surgical thread in conjunction with fifteen different cosmetic medical procedures are classified as:

(1) Six-dimensional barbed surgical thread and eight-dimensional barbed surgical thread exhibit similar performance to each other and superior performance when compared to the prior art four-dimensional barbed surgical thread (Table 1)

(2) Six-dimensional barbed surgical thread exhibits superior performance to the eight-dimensional barbed surgical thread and both the six-dimensional barbed surgical thread and the eight-dimensional barbed surgical thread exhibit superior performance to the prior art four-dimensional barbed surgical thread (Table 2).

(3) Eight-dimensional barbed surgical thread exhibits superior performance to the six-dimensional barbed surgical thread and both the six-dimensional barbed surgical thread and the eight-dimensional barbed surgical thread exhibit superior performance to the prior art four-dimensional barbed surgical thread (Table 3).

(4) Six-dimensional barbed surgical thread, eight-dimensional barbed surgical thread and the prior art four-dimensional barbed surgical thread exhibit similar performance to each other (Table 4).

TABLE 1

Similar Superior Performance of 6D and 8B Barbed Thread

| Treatment type | Description | 4D vs 6D Barb | 4D vs 8D Barb |
|---|---|---|---|
| Mid-Rhytidectomy | Midface to temple lift | significant | significant |
| Abdominplasty | Abdominal lift | moderate | moderate |
| Brachioplasty | Upper arm lift | moderate | moderate |
| Kneeplasty/Thighplasty | Knee/lower thigh lift | significant | significant |

TABLE 2

Superior Performance of 6D Barbed Thread

| Treatment type | Description | 4D vs 6D Barb | 4D vs 8D Barb |
|---|---|---|---|
| Nasolabial Folds Removal | Smile Lines | significant | moderate |
| Platysmaplasty | Neck Skin Tightening | significant | moderate |

TABLE 3

Superior Performance of 8D Barbed Thread

| Treatment type | Description | 4D vs 6D Barb | 4D vs 8D Barb |
|---|---|---|---|
| Lower Rhytidectomy | Jawline and neck lift | moderate | significant |
| Gyneocomastia | Male breast size reduction | minimal | moderate |
| Mastopexy Size > B+ | Breast lift | moderate | significant |
| Mastopexy Size > C+ | Breast lift | minimal | moderate |
| Gluteal Lift | Buttock lift | minimal | moderate |
| Jawline Contouring | Jowl lift | moderate | significant |

TABLE 4

Similar Performance of 6D, 8D and 4D Barbed Thread

| Treatment type | Description | 4D vs 6D Barb | 4D vs 8D Barb |
|---|---|---|---|
| Browplasty | Brow or forehead lift | no change | no change |
| Blepharoplasty | Eye hood lift | no change | no change |
| Mastopexy Size > D | Breast lift | no change | minimal |

In view of the fact that the six-dimensional barbed surgical thread and the eight-dimensional barbed surgical thread do not exhibit superior results to the prior art four-dimensional barbed surgical thread for all of the cosmetic medical procedures set forth in Tables 1-4 and in view of the fact that the six-dimensional barbed surgical thread and the eight-dimensional barbed surgical thread exhibit similar performance in certain cosmetic medical procedures but the six-dimensional barbed surgical thread provides superior results in some cosmetic medical procedures and inferior results in some cosmetic medical procedures as compared to the eight-dimensional barbed surgical thread indicate that the eight-dimensional barbed surgical thread is a not obvious modification of the prior art four-dimensional barbed surgical thread as well as the six-dimensional barbed surgical thread.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of using an eight-dimensional barbed surgical thread to perform one of a lower rhytidectomy, a gyneocomastia, a mastopexy with a breast size less than B+, a mastopexy with a breast size of less than C+, a gluteal lift, and jawline contouring, wherein the method comprises:
providing the eight-dimensional barbed surgical thread comprising a central core, eight first barbs and eight second barbs, wherein the central core has a circumference, a central core proximal end and a central core distal end that is opposite the central core proximal end, wherein the eight first barbs are positioned radially adjacent to each other around the circumference of the central core and obliquely extend from the central core, wherein each of the eight first barbs has a first barb distal end and a first barb proximal end, wherein each of the eight first barbs is oriented so that the first barb distal end is closer to the central core distal end than the first barb proximal end, wherein the eight second barbs are positioned radially adjacent to each other around the circumference of the central core and obliquely extend from the central core, wherein the eight second barbs are closer to the central core distal end than the eight first barbs, wherein each of the eight second barbs has a second barb distal end and a second barb proximal end and wherein each of the second barbs is oriented so that the second barb distal end is closer to the central core proximal end than the second barb proximal end; and
inserting the eight-dimensional barbed surgical thread into a dermis on a patient;
engaging the eight first barbs in the dermis to lift the dermis to a lifted position; and
engaging the eight second barbs in the dermis to anchor the dermis in the lifted position and complete the one of the lower rhytidectomy, the gyneocomastia, the mastopexy with the breast size less than B+, the mastopexy with the breast size of less than C+, the gluteal lift, and the jawline contouring.

2. The method of claim 1, wherein the eight first barbs occupy about ⅔ of a length of the eight-dimensional barbed surgical thread and wherein the eight second barbs occupy about ⅓ of the length of the eight-dimensional barbed surgical thread.

3. The method of claim 1, wherein adjacent barbs in the eight first barbs are offset in a direction extending between the proximal end and the distal end of the central core so that the first barb distal end of one of the eight first barbs is approximately aligned with the first barb proximal end of an adjacent one of the eight first barbs around a circumference of the central core and wherein every other of the eight first barbs is approximately aligned around a circumference of the central core.

4. The method of claim 1, wherein each of the eight first barbs occupies about 45 degrees of a circumference of the central core and wherein a cut is formed at an angle of between about 10 degrees and about 15 degrees with respect to a surface of the central core to form each of the eight first barbs.

5. The method of claim 1, wherein the eight-dimensional barbed surgical thread comprises a plurality of rows of the eight first barbs and wherein a spacing between the rows of the eight first barbs is less than about a length of one of the eight first barbs in a direction that extends between the central core proximal end and the central core distal end.

6. The method of claim 1, wherein the eight-dimensional barbed surgical thread is inserted into the dermis using a cannula.

7. The method of claim 6, wherein the cannula is rotated to cause the eight second barbs to engage the dermis.

8. The method of claim 1, wherein insertion of the eight-dimensional barbed surgical thread causes cellular renewal through collagen stimulation and neovascularization to improve skin texture.

9. The method of claim 1, wherein insertion of the eight-dimensional barbed surgical thread into the dermis causes skin tightening caused by contracting fat tissue.

10. The method of claim 1, wherein after anchoring the dermis in the lifted position, cutting off a portion of the proximal end of the eight-dimensional barbed surgical thread that extends through a skin surface on the person.

11. A method of performing one of a lower rhytidectomy, a gyneocomastia, a mastopexy with a breast size less than B+, a mastopexy with a breast size of less than C+, a gluteal lift, and jawline contouring, wherein the method comprises:
providing an eight-dimensional barbed surgical thread comprising a central core, eight first barbs and eight second barbs, wherein the central core has a circumference, a central core proximal end and a central core distal end that is opposite the central core proximal end, wherein the eight first barbs are positioned radially adjacent to each other around the circumference of the central core and obliquely extend from the central core, wherein each of the eight first barbs has a first barb distal end and a first barb proximal end, wherein each of first barbs is oriented so that the first barb distal end is closer to the central core distal end than the first barb proximal end, wherein the eight second barbs are positioned radially adjacent to each other around the circumference of the central core and obliquely extend from the central core, wherein the eight second barbs are closer to the central core distal end than the eight first barbs, wherein each of the eight second barbs has a second barb distal end and a second barb proximal end and wherein each of the second barbs is oriented so that the second barb distal end is closer to the central core proximal end than the second barb proximal end;
providing a cannula;
positioning the eight-dimensional surgical thread at least partially in the cannula;
inserting the cannula into the dermis;
remove the cannula from the dermis while leaving the eight-dimensional surgical thread at least partially in the dermis;
engaging the eight first barbs in the dermis to lift the dermis to a lifted position; and
engaging the eight second barbs in the dermis to anchor the dermis in the lifted position and complete the one of the lower rhytidectomy, the gyneocomastia, the mastopexy with the breast size less than B+, the mastopexy with the breast size of less than C+, the gluteal lift, and the jawline contouring.

12. The method of claim 11, wherein the cannula is rotated to cause the eight second barbs to engage the dermis.

13. The method of claim 11, wherein the cannula is a rounded or L-tipped surgical steel cannula.

14. The method of claim 11, wherein after anchoring the dermis in the lifted position, cutting off a portion of the proximal end of the eight-dimensional barbed surgical thread that extends through a surface of the skin.

* * * * *